US009476009B2

(12) United States Patent
Cairncross et al.

(10) Patent No.: US 9,476,009 B2
(45) Date of Patent: Oct. 25, 2016

(54) ACIDIC METHANOL STRIPPING PROCESS THAT REDUCES SULFUR CONTENT OF BIODIESEL FROM WASTE GREASES

(71) Applicants: Drexel University, Philadelphia, PA (US); Environmental Fuel Research, LLC, Philadelphia, PA (US)

(72) Inventors: Richard Allan Cairncross, Media, PA (US); Megan Elizabeth Hums, Philadelphia, PA (US); Colin James Stacy, Beaumont, TX (US)

(73) Assignees: Drexel University, Philadelphia, PA (US); Environmental Fuel Research, LLC, Philadelphia, PA (US)

( * ) Notice: Subject to any disclaimer, the term of this patent is extended or adjusted under 35 U.S.C. 154(b) by 0 days.

(21) Appl. No.: 14/690,909

(22) Filed: Apr. 20, 2015

(65) Prior Publication Data
US 2016/0257908 A1 Sep. 8, 2016

Related U.S. Application Data

(60) Provisional application No. 62/128,789, filed on Mar. 5, 2015.

(51) Int. Cl.
*C11C 3/00* (2006.01)
*C11C 3/10* (2006.01)
*C07C 67/08* (2006.01)

(52) U.S. Cl.
CPC .............. *C11C 3/003* (2013.01); *C07C 67/08* (2013.01); *C11C 3/10* (2013.01)

(58) Field of Classification Search
CPC ........ C11C 3/003; C07C 67/03; C07C 67/08
See application file for complete search history.

(56) References Cited

U.S. PATENT DOCUMENTS

| | | | |
|---|---|---|---|
| 4,668,439 A * | 5/1987 | Billenstein | C11C 3/04 554/167 |
| 4,698,186 A | 10/1987 | Jeromin et al. | |
| 5,939,571 A | 8/1999 | Foidl | |
| 7,767,839 B2 | 8/2010 | Berry et al. | |

(Continued)

FOREIGN PATENT DOCUMENTS

| | | | | |
|---|---|---|---|---|
| DE | 102007033310 A1 * | 1/2009 | ............. | C07C 67/03 |
| JP | 2009197081 A * | 9/2009 | ................ | C10L 1/02 |

(Continued)

OTHER PUBLICATIONS

Cairncross, R. et al., Novel Reactor Design for Biodiesel Production, Final Report, 2013, EPA: Research Grants/Fellowships/SBIR, 6 pages.*

(Continued)

*Primary Examiner* — Yate K Cutliff
(74) *Attorney, Agent, or Firm* — Mendelsohn Dunleavy, P.C.

(57) ABSTRACT

The present invention provides a method of producing fatty acid alkyl esters from a lipid, comprising steps of introducing a gas comprising vapor of an alcohol selected from methanol, ethanol, 1-propanol, iso-propanol and butanols, into the lipid in a form of bubbles to enable the bubbles to pass through the lipid and be discharged from the lipid. The product may then be subjected to a transesterification process catalyzed by a base catalyst. The present invention is robust with low quality feedstocks thus significantly reduce production cost for biodiesel.

20 Claims, 8 Drawing Sheets

(56) References Cited

U.S. PATENT DOCUMENTS

| | | | |
|---|---|---|---|
| 7,834,203 | B2 | 11/2010 | Lee et al. |
| 8,192,696 | B2 | 6/2012 | Gurski et al. |
| 8,585,901 | B1 | 11/2013 | Lenger et al. |
| 8,603,198 | B2 * | 12/2013 | Gordon ............... B01F 5/0644 366/176.1 |
| 2004/0059143 | A1 | 3/2004 | Peter et al. |
| 2010/0293840 | A1 | 11/2010 | Davies et al. |
| 2011/0179525 | A1 | 7/2011 | Messing et al. |
| 2011/0197497 | A1 | 8/2011 | Jiang |
| 2012/0030993 | A1 | 2/2012 | Crosier et al. |
| 2012/0255223 | A1 | 10/2012 | Kaul et al. |
| 2013/0239467 | A1 | 9/2013 | Lu et al. |
| 2014/0059922 | A1 | 3/2014 | Gordon et al. |

FOREIGN PATENT DOCUMENTS

| | | |
|---|---|---|
| WO | WO2012102757 A2 | 8/2012 |
| WO | WO2014039613 A1 | 3/2014 |

OTHER PUBLICATIONS

JP 2009197081 (A), Nabetani Koji, et al., Method for producing bio-diesel fuel, 2009, English translaiton, 14 pages.*

DE 102007033310 (A1), Richter, J., et al., Reducing acid number of fats or oils, comprises feedng the fats or oils and a homogeneous esterification catalyst in a counter flow esterification column and downwardly delivering fats or oils to reduce excess water and alcohol, 2009, English translation, 5 pages.*

Stacy, C.J., et al., Esterification of free fatty acids to fatty acid alkyl esters in a bubble column reactor for use as biodiesel, 2014, Fuel Processing TEchnology, vol. 124, pp. 70-77.*

Melick, C. A., Mohammed, M., & Cairncross, R. A. "Diseño de un Reactor para la Producción de Biodiesel de los Acidos Grasos," 2009, 5 pages, along with English abstract.

Hums, M.E, et al., "Feasibility and environmental impacts of the production of biodiesel from grease trap waste," Presented at the World Congress on Industrial Biotechnology, 2014, 1 page.

Chakrabarti, Alicia R., et al. "4Waste grease biodiesel production at a wastewater treatment plant." Proceedings of the Water Environment Federation 2008.14 (2008): 2770-2789.

"Process removes sulfur roadblock to grease to biofuel conversion," 2009, Retrieved from: http://www.waterworld.com/index/display/article-display/352133/articles/waterworld/environmental/process-removes-sulfur-roadblock-to-grease-tobiofuel-conversion.html.

Voegele, E., "Choosing the most appropriate feedstock pretreatment method for a given facility can make or break plant economics," Biodeisel Magazine, 2012, Retrieved from: http://www.biodieselmagazine.com/articles/8295/a-critical-component.

Austic, G. "Evaluating the profitability of a trap effluent dewatering facility in the Raleigh area," 2011, pp. 1-21.

"Out of the Frying Pan and into the Fuel Tank," Novel Reactor Design for Biodiesel Production, 2008, 1 page.

Kim, Manhoe, et al. "Performance of heterogeneous ZrO 2 supported metaloxide catalysts for brown grease esterification and sulfur removal." Bioresource technology 102.3 (2011): 2380-2386.

Kim, M., et al., "Sulfur Level Changes in Brown Grease Conversions with Sulfuric Acid and Heterogeneous Zirconia-Supported Metaloxides Catalysts," 2010 Annual Meeting, 3 pages.

Apostolakou, A. A., et al. "Techno-economic analysis of a biodiesel production process from vegetable oils." Fuel Processing Technology 90.7 (2009): 1023-1031.

Haas, M. J., "Improving the economics of biodiesel production through the use of low value lipids as feedstocks: vegetable oil soapstock," Fuel Processing Technology, 2005, 86, 1087-1096.

Marchetti, J. M., V. U. Miguel, and A. F. Errazu. "Techno-economic study of different alternatives for biodiesel production." Fuel Processing Technology 89.8 (2008): 740-748.

Zhang, Y. et al. "Biodiesel production from waste cooking oil: 1. Process design and technological assessment."Bioresource Technology 89 (2003): 1-16.

Zhang, Yea, et al. "Biodiesel production from waste cooking oil: 2. Economic assessment and sensitivity analysis."Bioresource technology 90.3 (2003): 229-240.

Canakci, Mustafa. "The potential of restaurant waste lipids as biodiesel feedstocks." Bioresource Technology 98.1 (2007): 183-190.

Van Gerpen, Jon. "Biodiesel processing and production." Fuel processing technology 86.10 (2005): 1097-1107.

Tyson, Karin Shaine, et al. Biomass oil analysis: research needs and recommendations. No. NREL/TP-510-34796. National Renewable Energy Lab Golden Co, 2004.

Berrios, M., et al. "A kinetic study of the esterification of free fatty acids (FFA) in sunflower oil." Fuel 86 (2007): 2383-2388.

Lucena, Izabelly L., et al. "Oleic acid esterification with ethanol under continuous water removal conditions." Fuel 90.2 (2011): 902-904.

Santacesaria, E., et al. "Comparison of Different Reactor Configurations for the Reduction of Free Acidity in Raw Materials for Biodiesel Production." Ind. Eng. Chem. Res 46 (2007): 8355-8362.

Wang, Zhong-Ming, et al. "Optimization of biodiesel production from trap grease via acid catalysis." Korean J. Chem. Eng 25.4 (2008): 670-674.

Kocsisová, Teodora, Ján Cvengros, and Juraj Lutišan. "High-temperature esterification of fatty acids with methanol at ambient pressure." European journal of lipid science and technology 107.2 (2005): 87-92.

"Brown Grease to Biodiesel Demonstration Project Report: Oceanside Water Pollution Control Plant," San Francisco Public Utilities Commission. No. CEC-500-2013-038. San Francisco Public Utilities Commission (SFPUC), 2012. 138 pages.

Stacy, Colin J., Cory A. Melick, and Richard A. Cairncross. "Esterification of free fatty acids to fatty acid alkyl esters in a bubble col. reactor for use as biodiesel." Fuel Processing Technology 124 (2014): 70-77.

Ndlovu, N., et al., "Effect of Different Acid Catalysts on Performance of a Bubble col. Reactor for Esterification of Waste Greases into Biodiesel," Drexel University, Department of Chemical and Biological Engineering, 2014, 1 pg.

He, B. B., J. H. Van Gerpen, and J. C. Thompson. "Sulfur content in selected oils and fats and their corresponding methyl esters." Applied Engineering in Agriculture 25.2 (2009): 223.

Hums, M.E., et al., "Longitudinal Study of Scum Grease for the Production of Biodiesel," PWD September Tech Talk, 2014, 1 page.

* cited by examiner

ACIDIC METHANOL STRIPPING PROCESS THAT REDUCES SULFUR CONTENT OF BIODIESEL FROM WASTE GREASES

STATEMENT OF FEDERALLY SPONSORED RESEARCH

This invention was made with government support under Contract No. EP-D-14-019 awarded by the Environmental Protection Agency. The government has certain rights in the invention.

BACKGROUND OF THE INVENTION

1. Field of the Invention

The present invention is directed to the field of producing biodiesel from a lipid. In particular, the present invention is directed to a process using a gaseous alcohol to convert a lipid to biodiesel and strip impurities from the lipid and/or biodiesel product.

2. Description of the Related Technology

There are many factors that have led to increased research into alternative fuels and renewable energy. Some of these factors include rising prices of crude petroleum, concerns about carbon dioxide emissions, worsening air quality by emissions of sulfur oxides, particle matter and other gases, as well as security of domestic energy supply coupled with limited long-term supplies of petroleum.

Biodiesel is a promising renewable fuel, which contains mostly fatty acid alkyl esters. Biodiesel is typically produced chemically by reacting plant or animal derived lipids with an alcohol. The majority of biodiesels are produced by reacting lipids with methanol to produce fatty acid methyl esters (FAME). Currently, most of the lipids for biodiesel production are refined lipids that have low free fatty acid (FFA) concentrations, such as soybean oil (in USA), rapeseed oil (in Europe), and palm oil (in Asia). However, these refined lipids are agricultural crops that are relatively high-cost, because their production requires significant fertilizer and chemical inputs.

Apostolakou et al. (Techno-economic analysis of a biodiesel production process from vegetable oils, *Fuel Processing Technology*, vol. 90, pages 1023-1031, 2009) and Haas (Improving the economics of biodiesel production through the use of low value lipids as feedstocks: vegetable oil soapstock, *Fuel Processing Technology*, vol. 86, pages 1087-1096, 2005) showed that the cost of raw materials can be 75%-90% of the cost of manufacturing biodiesel. Marchetti et al. (Techno-economic study of different alternatives for biodiesel production, *Fuel Processing Technology*, vol. 89, pages 740-748, 2008) discussed three scenarios for producing biodiesel from lipids containing 5% FFA. All three scenarios are profitable with raw materials being more than 80% of the manufacturing costs. Zhang et al. (Biodiesel production from waste cooking oil: 1. Process design and technological assessment, *Bioresource Technology*, vol. 89, pages 1-16 2003; and Biodiesel production from waste cooking oil: 2. Economic assessment and sensitivity analysis, *Bioresource Technology*, vol. 90, pages 229-240, 2003) compared four biodiesel production processes and found that the production of biodiesel from refined lipids had the lowest capital expense and highest cost of raw materials, while the processes converting waste lipids to biodiesel required higher costs on more methanol and larger distillation columns to recover unreacted methanol, though the cost on waste lipids is much lower. Because the feedstock is a major fraction of the biodiesel manufacturing costs, the process using low cost waste lipids will likely show much greater economic feasibility.

The costs of lipids are related to their FFA content. Edible lipids have low FFA content and command relatively high prices. Inedible lipids tend to be high in FFA and have low prices. The high-FFA lipids are mostly waste products and have limited commercial value, while low-FFA lipids tend to be viable food sources. For example, soybean oil currently sells for about $3.52 per gallon, and yellow grease (filtered and dewatered waste cooking oil with FFA content below 15%) sells for $2.19 per gallon. Trap grease is a potential source of high-FFA lipids, because wastewater utilities charge $0.06 or more per gallon to dispose of trap grease. Lipids separated from trap grease, which may be 2%-10% of the trap grease, can have over 95% FFA. Producing biodiesel from high-FFA lipids entails low feedstock costs and is less prone to controversies associated with producing fuels from food-grade lipids (M. Canakci, The potential of restaurant waste lipids as biodiesel feedstocks, *Bioresource Technology*, vol. 98, pages 183-190, 2007; and K. S. Tyson, DOE analysis of fuels and coproducts from lipids, *Fuel Processing Technology*, vol. 86, pages 1127-1136, 2005).

The high cost of the raw materials for biodiesel is one of the major reasons that biodiesel is not an ideal solution for the energy demand in the United States. Van Gerpen (Biodiesel processing and production, *Fuel Processing Technology*, vol. 86, pages 1097-1107, 2005) noted that only about 14% of current diesel demand can be replaced by biodiesel produced from crop-based lipids. If the cost of biodiesel production can be lowered by using low cost lipids, the production capacity of biodiesel may be expanded and biodiesel may become more widely used. The available feedstock for biodiesel production may double if waste greases are widely used for biodiesel production.

It has been proposed that high-FFA lipids such as waste lipid feedstocks can provide significant cost reduction and production capacity for biodiesel (Tyson et al., Biomass Oil Analysis: Research Needs and Recommendations, NREL, Golden Colo., 2004). There are several technologies available for converting high-FFA lipids to FAME. Acid-catalyzed esterification technology is effective for lipids over a large range of FFA concentrations. This technology is often used for pretreatment of lipids prior to base-catalyzed transesterification in a two-step process. A significant disadvantage of acid-catalyzed esterification is slower reactions. There are several ways to increase acid-catalyzed esterification reaction rates, including increasing temperature, increasing catalyst concentration, and removing by-product water.

For low FFA lipids (containing 1%-10% FFA), a two-step process including low-temperature acid-catalyzed esterification followed by base catalyzed transesterification is commonly used for converting the lipid to biodiesel. For lipids containing more than 50% FFA, a process with multiple moderate-pressure reactors with intermediate removal of water are used effectively for producing biodiesel (W. W. Berry, B. J. Ratigan, Process of making alkyl esters of free fatty acids, Philadelphia Fry-o-Diesel Inc., US, 2010). Multiple, identical reactors with intermediate water removal will increase reaction speed and conversion. But the process with multiple reactors also increases the capital and operating costs significantly. In addition, to achieve acceptable reaction speed, temperatures above the boiling point of methanol are often used, which requires elevated pressure to maintain methanol in the liquid phase. For example, Van Gerpen reports using 240° C. and 90 bar for such a process (Biodiesel processing and production, *Fuel Processing Technology*, vol. 86, pages 1097-1107, 2005) and Berry and Ratigan report 115° C. and 5.4 bar in a similar process (Process of making alkyl esters of free fatty acids, Philadelphia Fry-o-Diesel Inc., US, 2010). The heating and pressurizing of the reactor will also increase the operation costs.

Kocsisova et al. (High-temperature esterification of fatty acids with methanol at ambient pressure, *European Journal of Lipid Science and Technology*, vol. 107, pages 87-92, 2005) discloses a kinetic study of the acid-catalyzed esterification of free fatty acids with methanol at elevated temperatures above the boiling point of methanol, at ambient pressure, and at continual flow of liquid methanol into the reaction mixture. Under these conditions, the esterification reaction follows the rate equation for reactions of the first order. At temperatures that are 50-60° C. higher than the boiling point of methanol, the reaction rate is two to three times higher than at the temperatures close to the boiling point of methanol. Beside temperature, the reaction rate depends also on the flow rate of methanol and on the concentration of the catalyst. A high local molar excess of methanol in the input site with respect to FFA and effective removal of water from the reaction mixture also increase the reaction rate. High conversion of FFA to methyl esters (above 99%) with low residual acidity of the product (acid value around 2-3 mg KOH/g) is achieved in several tens of minutes at a low total molar ratio of methanol/FFA of around 3:1 to 4:1.

U.S. Pat. No. 8,603,198 discloses a method for producing fatty acid alkyl esters from lipids through transesterification and/or esterification using a flow-through cavitation device for generating cavitation bubbles in a fluidic reaction medium. The fluidic medium is passed through sequential compartments in the cavitation device having varying diameters and inner surface features to create localized reductions in fluid pressure thus vaporizing volatile alcohols in the medium to create volatile alcohol-filled bubbles, which provide an increased surface area and optimized conditions for the transesterification and/or esterification to occur at the gas-liquid interface. The method can produce fatty acid alkyl esters and a glycerol, with the former being used in biodiesel.

There is a need of a low cost and efficient process to convert lipids with high FFA concentration such as waste lipids to biodiesel. The present invention provides a method based on passing bubbles with an alcohol vapor through lipids with high concentrations of free fatty acids. The present invention has low energy cost and low feedstock cost, which results in producing biodiesel at a much lower cost. The low cost biodiesel will likely lead to wider applications for the biodiesel.

SUMMARY OF THE INVENTION

In one aspect, the present invention provides a method of producing fatty acid alkyl esters from a lipid, comprising steps of introducing a gas comprising vapor of an alcohol selected from methanol and ethanol into the lipid in a form of bubbles to enable the bubbles to pass through the lipid and be discharged from the lipid.

In another aspect, the method of the present invention further comprises recycling the alcohol in the discharged bubbles.

In yet another aspect, the method of the present invention further comprises adding an acid catalyst to the lipid and the acid catalyst may be selected from sulfonic acid, para-toluene sulfonic acid, sulfuric acid, methane sulfonic acid, and hydrochloric acid.

In another aspect, the method of the present invention further comprises subjecting the product of the introducing step to a transesterification process catalyzed by a base catalyst.

In some embodiments, the present invention provides a method of producing fatty acid alkyl esters from a lipid, comprising steps of introducing a gas comprising vapor of an alcohol into the lipid in a form of bubbles to enable the bubbles to pass through the lipid and be discharged from the lipid. The alcohol used may be selected from alcohols that are in a gaseous state at the temperature of the lipid.

In another aspect, the alcohol is selected from 1-propanol, iso-propanol and butanols.

In yet another aspect, the lipid is selected from trap grease, sewage scum grease, acid oils and other waste materials having a free fatty acid (FFA) content higher than 40%.

BRIEF DESCRIPTION OF THE DRAWINGS

FIG. 2A shows the remaining FFA in the lipid over time at different methanol flow rates. FIG. 2B represents the ratio of unreacted methanol exiting the bubble column reactor as a function of time with black dashed line indicating the time at which 95% conversion of FFA to FAME is achieved. FIG. 2C shows the effect of methanol flow rate on the time to reach 95% conversion of FFA to FAME (triangles, left axis) and excess methanol at 95% conversion of FFA to FAME (square, right axis).

FIG. 5A is the raw trap grease. FIG. 5B shows layers after heating and settling trap grease from top to bottom: lipid, floating solids, water, and sediment. FIG. 5C shows the lipid layer from trap grease in solid state at room-temperature. FIG. 5D shows the crude FAME obtained from the bubble column reactor according to one embodiment of the present invention in liquid state at room temperature.

DETAILED DESCRIPTION OF THE PREFERRED EMBODIMENT(S)

Figure 1:
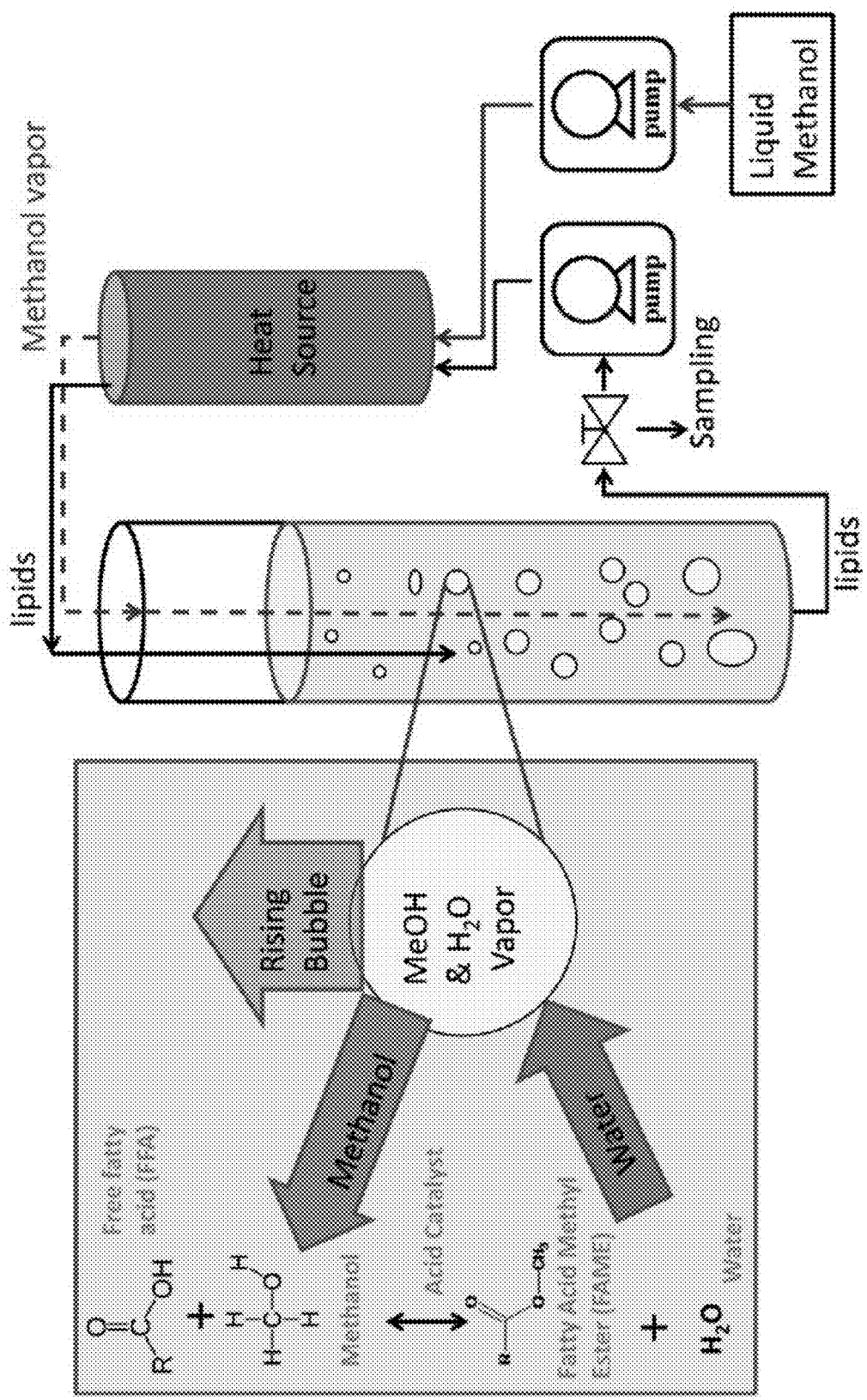
FIG. 1 is a schematic representation of one embodiment of the present invention showing bubbling action of methanol in a bubble column reactor filled with a lipid. The water and methanol transfer between lipid and vapor phase are also shown.

For illustrative purposes, the principles of the present disclosure are described by referencing various exemplary embodiments. Although certain embodiments are specifically described herein, one of ordinary skill in the art will readily recognize that the same principles are equally applicable to, and can be employed in other systems and methods. Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, any value within a disclosed range whether explicitly mentioned or not, as well as specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

Figure 6:
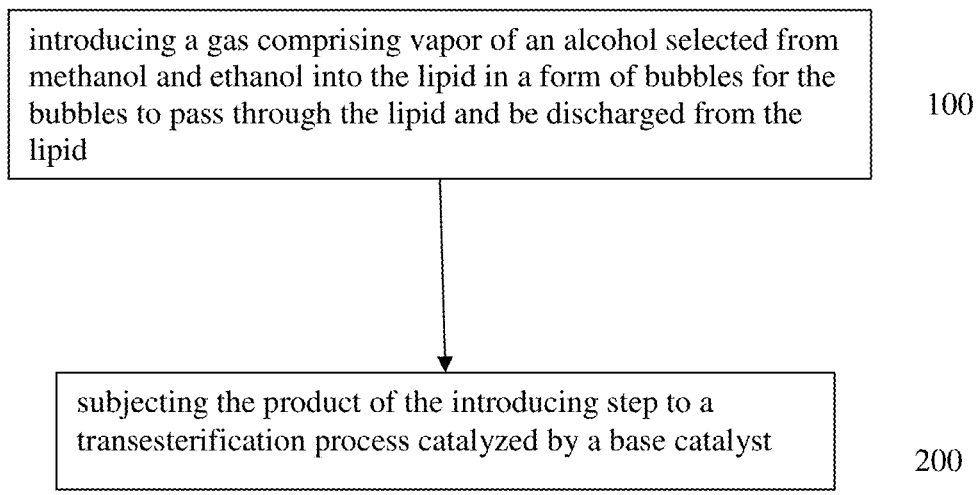
FIG. 6 is a flow chart showing a method of producing fatty acid alkyl esters from lipids according to one embodiment of the present invention.

The present invention provides a method for producing fatty acid alkyl esters from a lipid. Referring to FIG. 6, the method comprises the steps of introducing (100) a gas comprising vapor of an alcohol selected from methanol and ethanol into the lipid in a form of bubbles to enable the bubbles to pass through the lipid and be discharged from the lipid. The alcohol can esterify the FFA and/or transesterify triacyl glycerides in the lipid to produce fatty acid alkyl esters, which are used as biodiesel.

In some embodiments, the alcohol may be selected from 1-propanol, iso-propanol and butanols. In some embodiments, any alcohol with a boiling temperature below the reaction temperature of the present invention may be used.

To reduce cost of producing the fatty acid alkyl esters, the lipid is preferably selected from a low-value lipid obtained from non-food crops grown on marginal land (not land suitable for food crops) or from waste fats, waste greases, and waste oils. The lipid may have relatively high FFA content, for example at least about 10% FFA, or at least about 50% FFA, or at least 90% of FFA.

In some embodiments, lipid from trap grease may be used as the lipid feedstock for the present invention. Trap grease is a waste by-product of the food service industry that contains water, lipids, detergents, food particles and other waste. Trap grease is collected in grease interceptors, which are storage tanks ranging from a few gallons to several thousand gallons. Grease interceptors remove grease and sediments from kitchen effluent that could otherwise enter the sewage systems and cause blockages. Grease interceptors are required by law to be emptied at specific intervals, usually by commercial grease handlers, who are paid to pump and remove trap grease and then must pay to process and dispose of the grease properly. The lipids separated from trap grease may be used by the present invention as a lipid feedstock to produce fatty acid alkyl esters, which reduces the feedstock cost for biodiesel production to just a fraction of refined soybean lipids and other conventional sources of lipids for biodiesel production.

In some embodiments, other waste greases may also be used as feedstocks. Examples of these additional feedstocks include sewage scum grease (also called wastewater fats oils and greases (FOGs) or black grease), acid oils and other waste materials having a free fatty acid (FFA) content greater than 40% or by-products from processes selected from rendering processes, animal processing, vegetable oil separation and refining processes, biodiesel production processes.

In some embodiments, a bubble column reactor is used for the present invention, where the lipid is placed in the bubble column reactor and the bubbles with the alcohol pass through the lipid in the reactor, as show in FIG. 1. In one embodiment, the primary reaction chamber of the bubble column reactor may be a jacketed glass column with several pumps used for alcohol feeds and recirculation. Throughout this embodiment system, all parts exposed to reactants are made of glass, stainless steel, or PTFE.

As the bubbles pass through the lipid, some alcohol from the bubble may dissolve into the lipid though the solubility of the alcohol in lipids is small. The dissolved alcohol will react with the components (such as FFA and TAG) in the lipid. In addition, on the interface between bubbles and the lipid, reaction may also occur. There are two types of reactions that each can produce fatty acid alkyl esters. One is transesterification of triacyl glycerides (TAG), or triglycerides. During transesterification, a TAG molecule reacts with three alcohol molecules (such as methanol) to form three FAME molecules with by-product glycerin, as shown by the following reaction scheme:

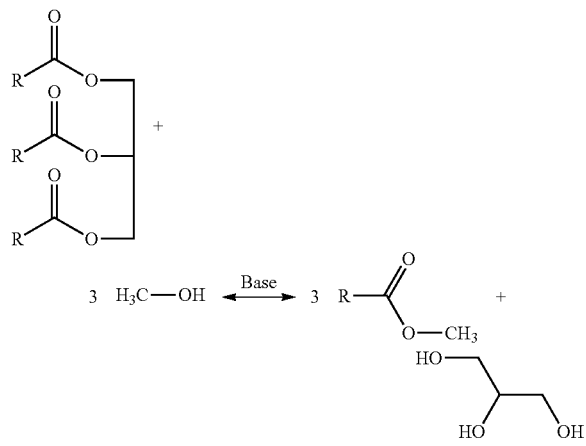

In this reaction equation, the alcohol is methanol, and R represents a long aliphatic fatty acid chain, which typically contains 8-22 carbon atoms (Samios et al., A transesterification double step process—TDSP for biodiesel preparation from fatty acids triglycerides, *Fuel Processing Technology*, vol. 90, pages 599-605, 2009). The transesterification reaction includes a series of three reactions in which TAG sequentially reacts with methanol molecules to form a diacyl glyceride molecule (DAG), a monoacyl glyceride (MAG), and finally glycerin with one FAME molecule produced at each step. Current industrial biodiesel processes predominantly use transesterification reaction catalyzed by base catalysts because this reaction requires low operating temperature and achieves high conversions within a couple of hours. However, the base catalyzed transesterification reaction requires the lipid to have high purity in TAG (low FFA content). When the FFA content in the lipid exceeds 1%, soaps may form from the reaction between the base catalyst and the FFA, which hinders transesterification and downstream purification of biodiesel (Ghadge et al., Biodiesel production from mahua (Madhuca indica) oil having high free fatty acids, *Biomass and Bioenergy*, vol. 28, pages 601-605, 2005; and Aryee et al., FTIR determination of free fatty acids in fish oils intended for biodiesel production, *Process Biochemistry*, vol. 44, pages 401-405, 2009). The alternative acid-catalyzed transesterification reaction does not form soaps even if FFA is present in the lipid at a significant level. But acid-catalyzed transesterification reaction is much slower than base catalyzed transesterification reaction and require higher temperature to achieve reasonable conversion rates (Van Gerpen, Biodiesel processing and production, *Fuel Processing Technology*, vol. 86, pages 1097-1107, 2005; and Varanda et al., Life cycle analysis of biodiesel production, *Fuel Processing Technology*, vol. 92, pages 1087-1094, 2011).

For the FFA in the lipids, acid-catalyzed esterification is effective for producing FAME from FFA:

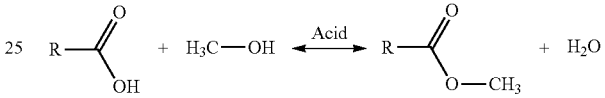

This esterification of FFA is catalyzed by acids like sulfuric acid. Many acids have been described previously that are capable—to catalyze esterification of FFA (Ghadge et al., Biodiesel production from mahua (*Madhuca indica*) oil having high free fatty acids, *Biomass and Bioenergy*, vol. 28, pages 601-605, 2005; Berrios et al., A kinetic study of the esterification of free fatty acids (FFA) in sunflower oil, *Fuel*, vol. 86, pages 2383-2388, 2007; Kocsisova et al., High-temperature esterification of fatty acids with methanol at ambient pressure, *European Journal of Lipid Science and Technology*, vol. 107, pages 87-92, 2005; Lucena et al., Oleic acid esterification with ethanol under continuous water removal conditions, *Fuel, vol.* 90, pages 902-904, 2011; Santacesaria et al., Comparison of different reactor configurations for the reduction of free acidity in raw materials for biodiesel production, *Industrial & Engineering Chemistry Research*, vol. 46, pages 8355-8362, 2007; Voll et al., Thermodynamic analysis of fatty acid esterification for fatty acid alkyl esters production, *Biomass and Bioenergy*, vol. 35, pages 781-788, 2011; Wang et al., Optimization of biodiesel production from trap grease via acid catalysis, *Korean Journal of Chemical Engineering*, vol. 25, pages 670-674, 2008; Wahlen et al., Synthesis of biodiesel from mixed feedstocks and longer chain alcohols using an acid-catalyzed method, *Energy & Fuels*, vol. 22, pages 4223-4228, 2008).

The esterification reaction produces water as a by-product. Esterification reaction is reversible and equilibrium-limited by the accumulation of the water by-product. The presence of water generally reduces the conversion rate of FFA to fatty acid alkyl ester in comparison with the reaction when water is not present. Continuously removal of water by-product from the reaction product has been shown to dramatically increase yields of the fatty acid alkyl ester (Lucena et al., Oleic acid esterification with ethanol under continuous water removal conditions, *Fuel*, vol. 90, pages 902-904, 2011). As shown in FIG. 1, the water by-product formed by the esterification reaction can evaporate back into the bubbles and be removed by the bubbles from the lipid as the bubbles exit from the lipid. Thus, the present invention is effective at continuously removing water from the system by the bubbles, which results in high yields of fatty acid alkyl ester.

Surprisingly, the present invention can also reduce the sulfur content in the biodiesel produced using the present invention. Without being bound by theory, the alcohol (such as methanol) from the bubbles can also convert the sulfur-containing components of the lipid to intermediates that can either vaporize and be stripped from the lipid by the bubbles or are water soluble which can easily be washed away by water at a late stage. The present invention also has the advantage of tolerating sulfur impurities in the acid catalyst because the alcohol is effective in removing or helping to remove the sulfur-containing components from the reaction mixture in the bubble column reactor.

The bubbles exiting the lipid may still contain some unreacted alcohol, along with water vapor. The unreacted alcohol may be recycled for use in the introducing step 100. For example, the alcohol may be collected using a condenser.

Referring to FIG. 1, the alcohol may be converted to vapor by using a heat source. The heat source can heat a liquid alcohol to a temperature that is sufficient to convert the liquid alcohol to gas vapor. The gas vapor of the alcohol is then introduced into the lipid as bubbles that pass through the lipid.

A person skilled in the art will appreciate that high temperature may accelerate the transesterification reaction and/or esterification reaction between the alcohol and the lipid. In some embodiments, the lipid in the reactor is heated to a temperature of about 120° C. to shorten the reaction time.

Strong acids such as sulfonic acid, sulfuric acid, methane sulfonic acid, hydrochloric acid, or p-toluene sulfonic acid are used as catalyst at a concentration in the lipid in a range of from about 0.01% (w/w) to 2.0% (w/w) of the lipid. In one embodiment, the acid at a concentration of about 0.1% (w/w) of the lipid is used. In some embodiments, the catalyst is mixed with an alcohol to form a catalyst solution. This solution may then be gradually added to the lipid by a peristaltic pump during the first 5 min of the reaction.

The bubbles comprising alcohol vapor pass through the lipid to provide alcohol for the esterification and/or transesterification reactions. Higher flow rate for the alcohol affords more reactant thus accelerating the reactions. The flow rate of the alcohol through the lipid may be from about 0.20 mL/min to about 3.5 mL/min, or from about 0.43 mL/min to about 2.57 mL/min, or from about 0.75 mL/min to about 1.75 mL/min, or from about 0.75 mL/min to about 1.16 mL/min.

In some embodiments, the time period for reacting the alcohol as gas bubbles passing through the lipid is from about 6.2 minutes to about 113.5 minutes, or from about 8.7 minutes to about 52.5 minutes, or from about 12.3 minutes to about 29.1 minutes, or from about 12.3 minutes to about 19.1 minutes.

In some embodiments, the reactor for producing fatter acid alkyl esters is a bubble column reactor. The bubble column reactor may be constructed as a jacketed glass column 18-in. tall with a 1-in. internal diameter. Typically, the reactor operates at a temperature of about 120° C. with about 180 mL, or 400 mL, or 1500 mL, or 4000 mL of feedstock lipids. The bubble column reactor and the alcohol-vaporizer/lipid-reheater (FIG. 1) may be heated by circulating hot silicone oil from a heating bath. In some embodiments, mineral oil or vegetable oil may also be used in the heating bath. In some other embodiments, a heating element is used to enclose the bubble column reactor to heat the enclosed reactor. The top of the reactor may be open to the atmosphere, which allows the alcohol and water vapor bubbling through the lipid in the reactor to exit the reactor. The interior of the reactor has stainless steel tubing to transport chemicals into and out of the reactor and stainless steel-cladded thermocouples to monitor the reactor temperature. The glass column may be topped with a glass funnel that prevented overflow of the lipid during bubbling. Preferably, the gas bubbles comprising the alcohol vapor enter the reactor through an inlet at or near the bottom of the reactor.

In some embodiments, the lipid in the reactor may be circulated from the bottom of the reactor to the top of the reactor through an external sampling loop. Before returning to the top of the reactor, the circulating lipids passes through heat exchanger tubes immersed in hot silicone oil to maintain the temperature of the lipid. This same heat exchanger may also be used to heat and vaporize the alcohol feed, which is fed to the heat exchanger as a liquid by syringe pumps and vaporized in separate tubes in the heat exchanger before being introduced to the reactor. Two syringe pumps may be used sequentially during the process where one syringe pump is filled with alcohol while the other can discharge alcohol into the reactor through the heat exchanger.

Kocsisova et al. (High-temperature esterification of fatty acids with methanol at ambient pressure, *European Journal of Lipid Science and Technology*, vol. 107, pages 87-92, 2005) teaches that methanol should be fed to a reactor as a liquid. However, feeding liquid methanol to the reactor caused a drop in reactor temperature due to the latent heat of vaporization of methanol to create bubbles in the lipid. The present invention feeds the alcohol to the lipid directly as a vapor, which leads to more stable temperatures in the lipid.

The present invention converts free fatty acids to fatty acid alkyl esters (for use as biodiesel) at a conversion rate of over 95% of free fatty acid in less than 2 h under a variety of reaction conditions. For example, with a sulfuric acid catalyst concentration of 0.1 wt %, a reaction temperature of about 120° C. and ambient pressure, a methanol to fatty acid molar ratio of less than 3:1, and bubbling methanol vapor through the reactor at a flow rate of 0.034 moles of alcohol per mole of FFA per minute into liquid, the time to 95% conversion for the FFA is about 70 min. At higher methanol flow rates, the time to 95% conversion for the FFA may decrease to about 40 min but requires a methanol to fatty acid molar ratio of 5:1 or higher, which may lead to more unreacted methanol in the bubbles exiting the lipid.

The alcohol may be pure methanol or ethanol, or pure propanols or pure butanols. In some embodiments, there may be up to about 10%, or up to about 20% water in the liquid alcohol that is used to generate vapor to be introduced into the lipid. In one embodiment, the liquid alcohol contains methanol and water at about 90:10 ratio, or about 80:20 ratio. In one embodiment, the liquid alcohol contains ethanol and water at about 90:10 ratio, or about 80:20 ratio.

The present invention can use low-quality alcohol feedstocks that contain water. Thus, the invention is potentially useful for the conversion of low-value lipids into biodiesel using low-quality alcohols such as ethanol produced from biomass, which can lower the feedstock costs for the biodiesel production processes. As a result, the cost of producing biodiesel from renewable resources could be lowered substantially. The present invention has several other potential advantages related to sustainability including: flexibility to varying FFA content, flexibility for alcohol feed, robustness to moisture, and reduced energy requirements. The present invention is a robust method that can handle a variety of feedstocks without additional pretreatment, which will reduce economic hurdles to construct and operate biodiesel production facilities and result in lower consumer prices of biodiesel products.

The transesterification reaction is low when the catalyst is an acid catalyst, as described herein. Therefore, at the end of the introducing step 100, though almost all of FFA has been converted to fatty acid alkyl esters, the TAG in the lipid may not have achieved complete conversion. However, the product of the introducing step 100 has very low FFA Referring to FIG. 6, the product from the introducing step 100 can be subjected to a transesterification process 200 catalyzed by a base catalyst.

The transesterification process uses an alcohol, preferably methanol or ethanol, to convert TAG to fatty acid alkyl esters and glycerin, as shown below:

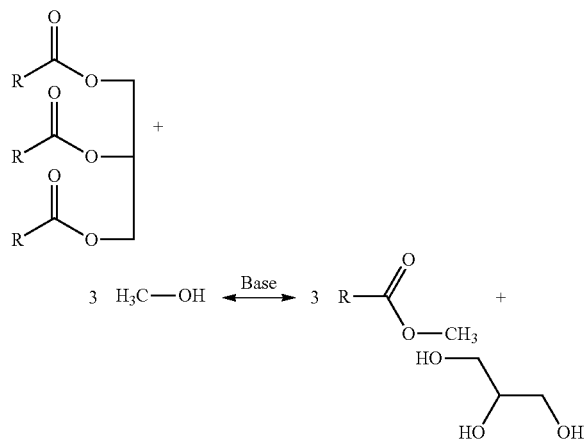

In this reaction equation, methanol is used. The catalyst for this transesterification process is a case catalyst, typically strong bases. The transesterification process is described in details in Samios et al., A transesterification double step process—TDSP for biodiesel preparation from fatty acids triglycerides, *Fuel Processing Technology*, vol. 90, pages 599-605, 2009, which is hereby incorporated herein by reference in its entirety.

This two-step process can utilize any renewable lipid resource that contains FFA and TAG in any ratio. Because the present invention does not require temperatures or pressures as high as other esterification methods, it may prove to be a cost effective esterification step in a two-step conversion both FFA and TAG to fatty acid alkyl esters. This robustness of the method with respect to lipid feedstocks and alcohol feedstocks allows biodiesel manufacturers employing this technology to greatly diminish their feedstock costs. Because feedstock costs are a dominant expense in producing biodiesel, it could lower the price of biodiesel to a level that is more competitive with petroleum diesel.

EXAMPLES

The following examples are illustrative, but not limiting, of the methods and compositions of the present disclosure. Other suitable modifications and adaptations of the variety of conditions and parameters normally encountered in the field, and which are obvious to those skilled in the art, are within the scope of the disclosure.

Example 1

Oleic acid was used to model a lipid feedstock with FFA for this example. Oleic acid at technical grade purity (N90%) as well as toluene and methanol with purities above 99% were purchased from Sigma Aldrich and used without further purification. Ethanol was anhydrous and denatured with 5% isopropyl alcohol and was also purchased from Sigma Aldrich. Isopropyl alcohol was purchased from Azer Scientific and was 99.99% purity. Sulfuric acid at 93% weight (66° Baume) was purchased from Fischer Scientific. Paratoluene sulfonic acid (PTSA) was purchased from Sigma-Aldrich and dissolved in methanol for use. Triglyceride samples were refined soybean oil purchased from local supermarkets. Trap grease was donated by Russell Reid waste management.

The conversion of fatty acid chains to FAME was quantified using two techniques: (1) base titration and (2) and nuclear magnetic resonance (NMR). The titrant used was a 0.1 molar solution of sodium hydroxide in methanol, and samples from the reactor were dissolved in a titration solution containing equal parts toluene and isopropyl alcohol with trace phenolphthalein as an indicator; this is a titration procedure similar to AOCS Cd 3d-63 and ASTM D-664. The base titrant was prepared from a standard base concentrate (Fixanal purchased from Sigma Aldrich) and tested against an acid standard prior to experimentation. This titration determined the acid number of the sample (mg KOH/g sample). For samples where the average molecular weight of the fatty acid is known (for example, oleic acid), the molar fraction of FFA was readily determined.

For experiments with partial TAG feedstocks, titration cannot completely determine the conversion rate of fatty acid to FAME. So proton NMR (H-NMR) spectroscopy was used to measure the FAME content of samples over time. The machine used for analysis of FAME samples was Drexel University's 500 MHz Inova Varian NMR. H-NMR peaks were assigned to their appropriate functional groups as shown in the supplementary documentation. A combination of NMR and titration enables determining the content of FFA, FAME, and acyl glyceride fatty acids.

The experimental conditions for this example were as follows: a reactor temperature of 120° C., ambient pressure, lipid volume of 180 mL of pure oleic acid, alcohol feed at 0.75 mL of liquid methanol per minute, and 0.1% (wt. catalyst/wt. lipids) of sulfuric acid catalyst added during first 5 min of reaction. Deviations from these conditions are indicated when used. Oleic acid was used as the FFA for these experiments as an appropriate surrogate for naturally occurring FFA. The catalyst concentration of 0.1% (w/w) sulfuric acid was used for this example.

Figure 2A:
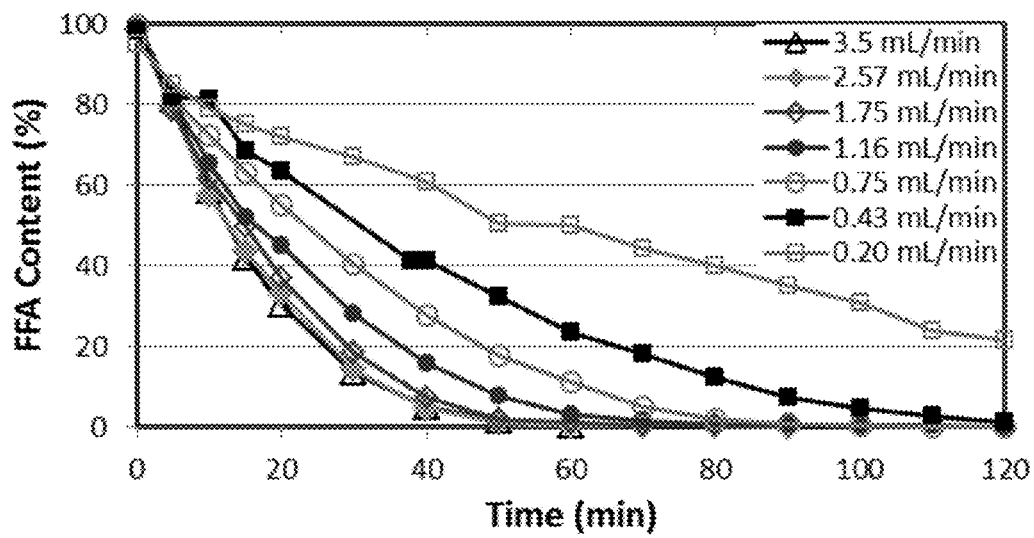
FIGS. 2A-2C show the effect of methanol flow rate on conversion of FFA to FAME in a bubble column reactor according to one embodiment of the present invention.
Figure 2B:
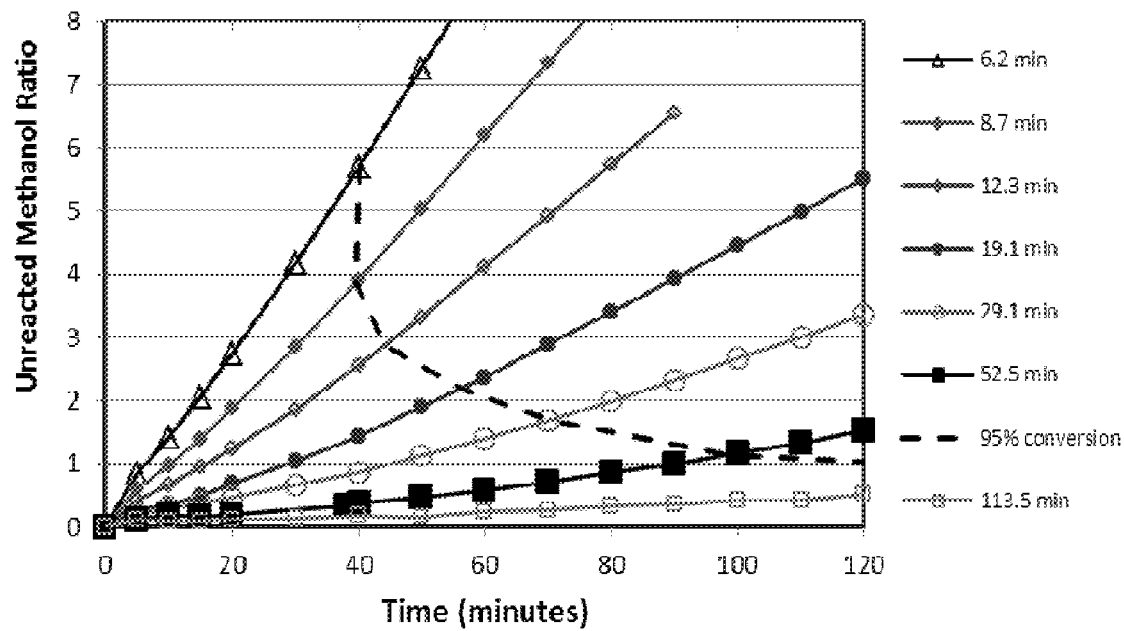
Figure 2C:
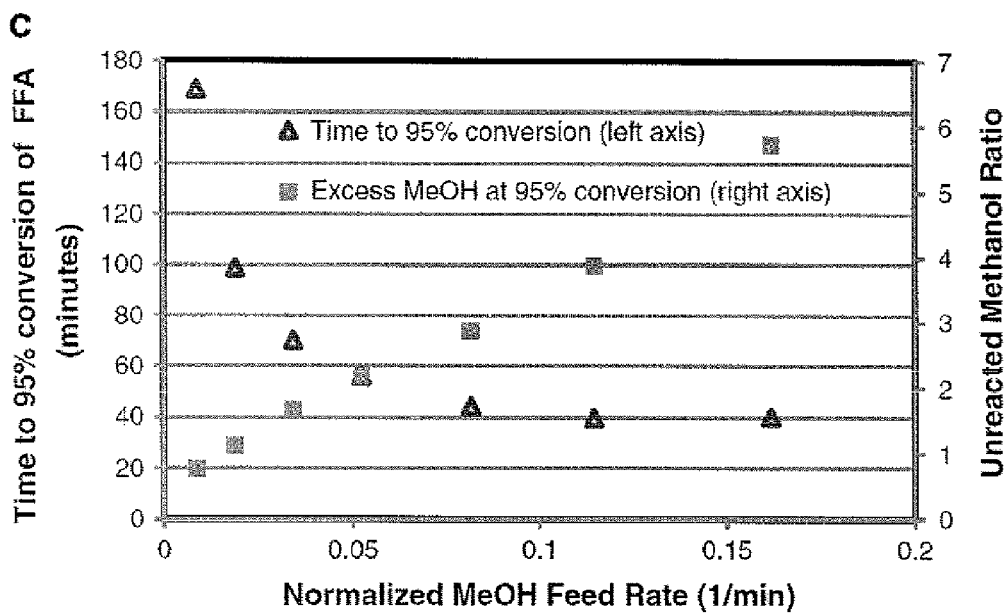

Methanol was continuously fed to the bubble column reactor filled with FFA (oleic acid) by syringe pumps. The effect of methanol feed rate to the reactor on conversion of FFA to FAME is shown in FIGS. 2A-2C. The syringe pumps fed liquid methanol, which was vaporized by the heat exchanger before reaching the reactor. The methanol flow rates were indicated as liquid milliliters per minute at which the syringe pumps operated. Alternative ways of showing flow rates are shown in Table 1.

FIG. 2A shows that as the reaction proceeded, the amount of FFA in the reactor decreased rapidly at first and later asymptotically approached zero. The rate at which FFA decreased, or the slope of the conversion profile, varied with the flow rate of methanol in the reactor with higher initial slopes corresponding to higher methanol flow rates. At methanol flow rates higher than 1.16 mL/min (for 180 mL of FFA in reactor), conversion of greater than 95% of FFA to FAME was achieved in less than 60 min. As the flow rate of methanol decreased, so did the reaction rate. At flow rates of less than 0.43 mL/min, 95% conversion of FFA to FAME took more than 100 min.

In FIG. 2A, the conversion profiles for the lowest methanol flow rates are nearly linear because the supply of methanol limited the reaction rate. In the low methanol flow rate reactions, the measured decrease in concentration of FFA was close to the moles of methanol fed to the reactor divided by the volume of lipids in the reactor. Thus, nearly all the methanol fed to the reactor reacted with FFA to produce FAME. Because the cumulative amount of methanol fed to the reactor is linear with time at low flow rates, the measured FFA content decreases nearly linearly with time due to a limited supply of methanol.

As the flow rate increased, the reaction rate increased until the reaction approached an apparently kinetically limited regime. Faster methanol flow rates created more vigorous bubbling, which leads to a reduction in mass transfer resistance and contributed to faster reaction rates and faster decrease of FFA content in the lipid as shown in FIGS. 2A-2C. For methanol flow rates higher than 2.57 mL/min, the reaction rate was independent of the flow rate, which indicates that for these reaction conditions, the reaction kinetics had a dominant effect on the conversion profile.

Table 1 contains alternative expressions of those flow rates that may be useful for interpreting the results. The first column in Table 1 is the liquid methanol flow rates in milliliters per minute. The second column shows the flow rate of methanol in moles of methanol per minute. The third column shows the molar flow rate of methanol that is scaled by the initial moles of oleic acid in the reactor. This is a normalized flow rate expressed in inverse minutes. This normalized flow rate is useful in representing how much methanol is available to react with the oleic acid in the reactor. The normalized flow rate is also useful for scaling between reactors with different volumes of FFA. The fourth column is the reciprocal of the third column and is the time required for the moles of methanol fed to the reactor to be equal to the initial moles of oleic acid in the reactor. This is the theoretical minimum time for complete conversion if all methanol entering the reactor reacted with oleic acid to produce FAME.

TABLE 1

Representations for alcohol flow rates for experiments shown in FIGS. 2A-2C

| Volumetric flow rate of liquid MeOH (mL/mon) | Molar flow rate of MeOH (mol/min) | MeOH flow normalized by $FFA_0$ (1/min) | Time to stoichiometric delivery of MeOH (min) |
|---|---|---|---|
| 3.5 | 0.0859 | 0.1617 | 6.2 |
| 2.57 | 0.0631 | 0.1146 | 8.7 |
| 1.75 | 0.0430 | 0.0816 | 12.3 |
| 1.16 | 0.0285 | 0.0523 | 19.1 |
| 0.75 | 0.0184 | 0.0343 | 29.1 |
| 0.43 | 0.0106 | 0.0190 | 52.5 |
| 0.2 | 0.0049 | 0.0088 | 113.5 |

At some methanol flow rates, some methanol passed through the reactor without reacting with FFA to form FAME. The ratio of the unreacted methanol to the initial amount of FFA in the reactor is the "unreacted methanol ratio." The unreacted methanol in bubbles exiting the reactor may be vented to a fume hood. This unreacted methanol could be collected and recycled, which is especially important for full scale production processes. The amount of unreacted methanol was calculated from the known methanol flow rate and the measured conversion of FFA to FAME:

$$\text{Unreacted methanol ratio} = \frac{\dot{N}_{MeOH} * t + N_{FFA}(t)}{N_{FFA,0}} - 1$$

where $N_{MeOH}$ is the molar flow rate of methanol, $N_{FFA(t)}$ is the moles of FFA in the reactor at time t measured by titration, and $N_{FFA,0}$ is the initial number of moles of FFA. FIG. 2B plots the data of FIG. 2A as unreacted methanol verses time with methanol flowrate indicated as time to stoichiometric delivery of methanol (last column of Table 1).

At low methanol flow rates, the unreacted methanol in the bubble exiting the reactor was close to zero, which means that most of the methanol fed to the reactor reacted with FFA to produce FAME, i.e., the methanol used is close to the stoichiometric ratio of methanol to FAME. As the methanol flow rate increased, unreacted methanol in the bubble exiting the reactor increased to over eight times the stoichiometric ratio of methanol required. In all cases, the unreacted methanol was initially lower and increases approximately linearly at long times. At long times, the esterification reaction rate approached zero. Thus nearly all of the methanol that entered the reactor passed through the lipid unreacted, leading to a linear increase in unreacted methanol. The dashed curve of FIG. 2B indicates the time at which each experiment achieves 95% conversion of FFA to FAME. The lower methanol flow rates correspond to both lower fractions of unreacted methanol and longer time to reach 95% conversion of FFA to FAME.

FIG. 2A shows that higher methanol flow rates lead to faster reaction rates, and FIG. 2B shows that higher methanol flow rates also lead to a high excess of methanol fed through the reactor. As the flow rate decreased, both of these quantities decrease. Consequently, there is an important trade-off in a bubble column reactor: between short reaction time and high methanol excess. At high methanol excess, the amount of methanol used and the cost of equipment required to collect, separate, and recycle excess methanol increases. At low reaction rates, the rate of FAME production per unit volume of reactor is small, so larger reactors are required. It is desirable to find a balance between low methanol excess and fast reaction rate.

FIG. 2C plots an alternative representation of the reaction conversion data as the time required to reach 95% conversion of FFA to FAME (t95) and the fractional unreacted methanol at 95% conversion as functions of flow rate. At low methanol flow rates, t95 increases hyperbolically as flow rate decreases. At high methanol flow rates, t95 asymptotically approaches a constant value of about 40 min. So for a pure methanol feed at 120° C. in this reactor configuration, 40 min is the shortest time to reach 95% conversion of oleic acid to FAME. The unreacted methanol ratio at 95% conversion is a function that is nearly linear with respect to methanol flow rate. In FIG. 2C, the far-left and far-right regions are regions where the reactions have either low conversion rate or high excess of methanol. The middle region of FIG. 2C may be the region with the most desirable flow rates that balance the trade-off between faster reactions (smaller reactor at high flow rates) and lower unreacted methanol (less excess methanol that has to be recovered and recycled).

Figure 3:
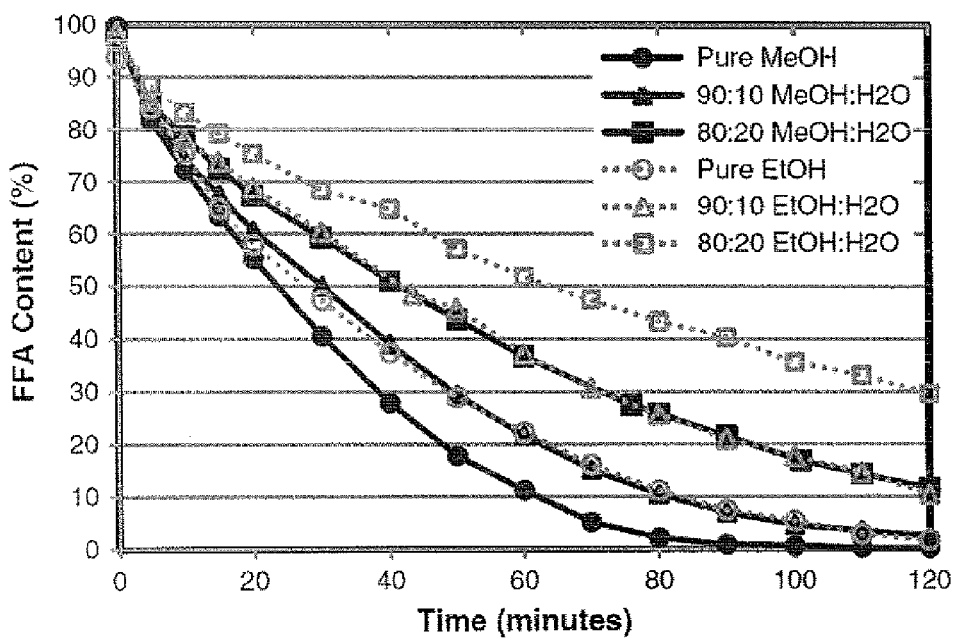
FIG. 3 shows the change of FFA content in the lipid during reactions in a bubble column reactor according to one embodiment of the present invention, using different alcohols with varying water content (on a volume basis). Methanol (MeOH) and ethanol (EtOH) were used with a constant catalyst concentration and a constant alcohol flow rate of 0.75 mL/min.

FIG. 3 displays FFA conversion profiles for a series of reactions that were performed with different alcohol feedstocks. Both ethanol (EtOH) and methanol (MeOH) were used as primary alcohols. The alcohol was also mixed with water in concentrations of 90:10 and 80:20 alcohol:water by volume as alcohol feedstocks. In typical esterification reaction of FFA, water hinders the esterification reactions of FFA because water is a by-product and enhances the reverse reaction. However, in the bubble column, rising methanol vapor bubbles strip water from the lipids and remove the water out of the lipid. This allows high conversions of FFA to FAME to be obtained with alcohol feedstocks containing in excess of 10% water by volume.

The reaction profiles in FIG. 3 show that reaction rates were lower in experiments with water-diluted alcohols. The decrease in the reaction rate is likely because as alcohol flow rates were maintained at the same volumetric rate but lower alcohol purity, the molar feed rate of alcohol is reduced. For example, FIG. 3 shows that an increase from 0% to 10% water in the alcohol feed lengthens the time to 90% conversion from 60 to 80 min for methanol and from 80 to 120 min for ethanol. Also, the conversion profiles in FIG. 3 show that all of the reactions with methanol proceed faster than reactions with ethanol at the same volumetric water concentration.

Surprisingly, the conversion profile for pure ethanol feed was nearly the same as the conversion for methanol feed with 10% water; likewise, the profile for ethanol with 10% water overlaps the profile for methanol for 20% water. Hence, under these conditions, switching from methanol to ethanol had roughly the same effect on conversion time as adding 10% water by volume to the methanol feed.

The use of different types of alcohol feedstock and alcohol moisture content (displayed in FIG. 3) demonstrated that the fastest esterification reactions used pure methanol as the alcohol feedstock. However, the bubble column reactor is robust and achieved a high conversion of FFA to FAAE for varying alcohol feeds and with lower quality alcohol feedstocks containing water. If the reactor can utilize lower-quality alcohol feedstocks, then the cost of raw materials for making FAAE can be reduced. Additionally, the cost of recycling the alcohol/water bubbles exiting from the reactor can be reduced because it is not necessary that the recycled alcohol be completely free of water, possibly eliminating the need to break any alcohol/water azeotropes.

In addition to being robust for impure feeds, this example shows that larger alcohols (such as ethanol) can react with fats, greases, and oils for FAAE production in the bubble column. Using ethanol as the alcohol feedstock could have several advantages, including the potential to be produced from renewable feedstocks and having lower toxicity than methanol.

Example 2

Figure 4A:
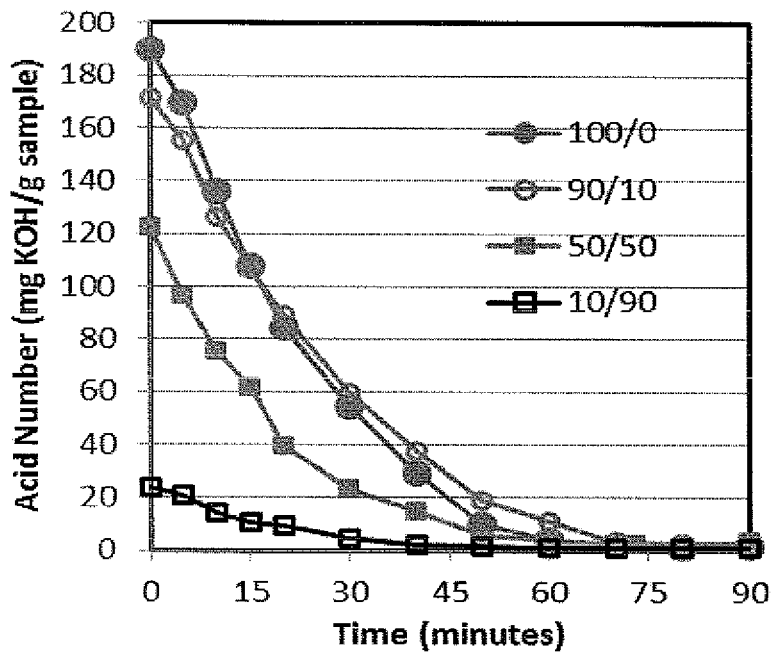
FIG. 4A shows acid numbers in lipids with different mixing ratios of FFA and triacyl glycerides (TAG) (v/v %). The acid numbers are reduced over time as methanol bubbles through the lipid in a bubble column reactor according to one embodiment of the present invention.
Figure 4B:
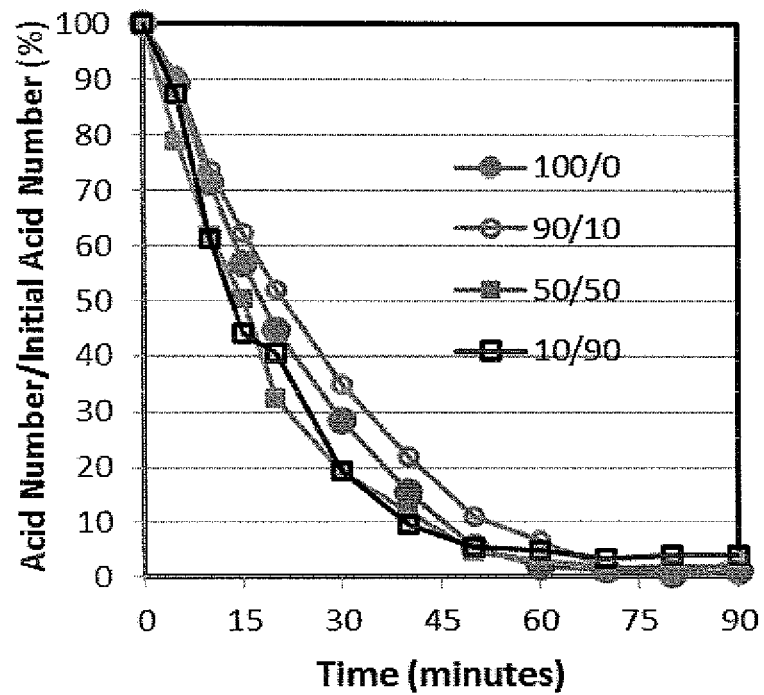
FIG. 4B shows the same data in FIG. 4A, but the y-axis indicates the percentage reduction of initial acid number.

In this example, the lipid is a mixture of FFA and TAG at different ratio (v/v %) from 100:0 to 10:90. This example is for examining the performance of the bubble column reactor for creating FAME using feedstocks containing a mixture of FFA and TAG. The FAME, FFA, and TAG content were analyzed using titration and NMR. FIG. 4A plots changes in acid number versus time for several experiments with different initial FFA content, which follows the pattern of an exponential decay, similar to that of pure FFA experiments. The data showed that after about 70 min, more than 95% of the initial FFA is converted to FAME. FIG. 4B shows the percent change of acid number normalized to the initial acid number of the reactions in FIG. 4A. The curves in FIG. 4B show that conversion profiles for the esterification of FFA collapse to a "master curve" when normalized to initial acid number.

Figure 4C:
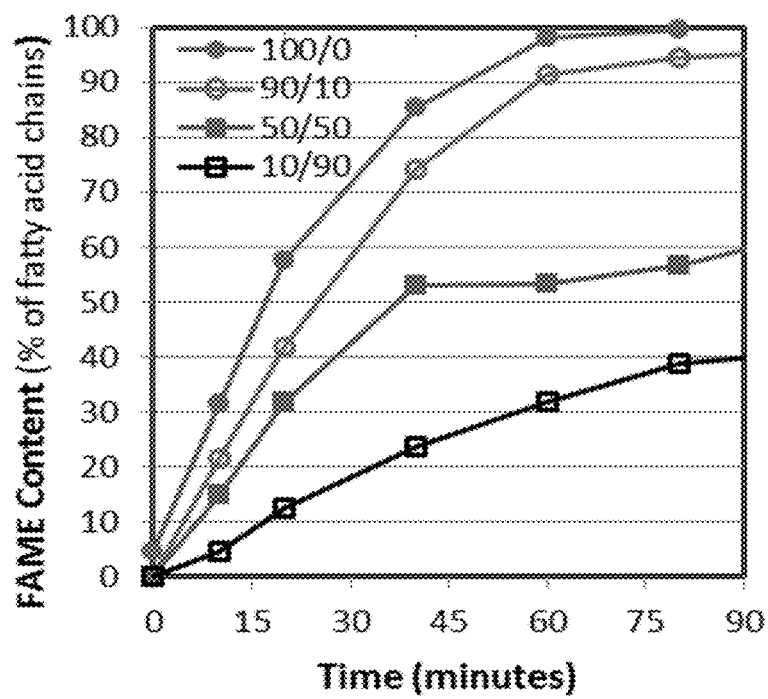
FIG. 4C shows the content of FAME in the lipid over time as measured by nuclear magnetic resonance (NMR), in the same experiment of FIG. 4A.
Figure 4D:
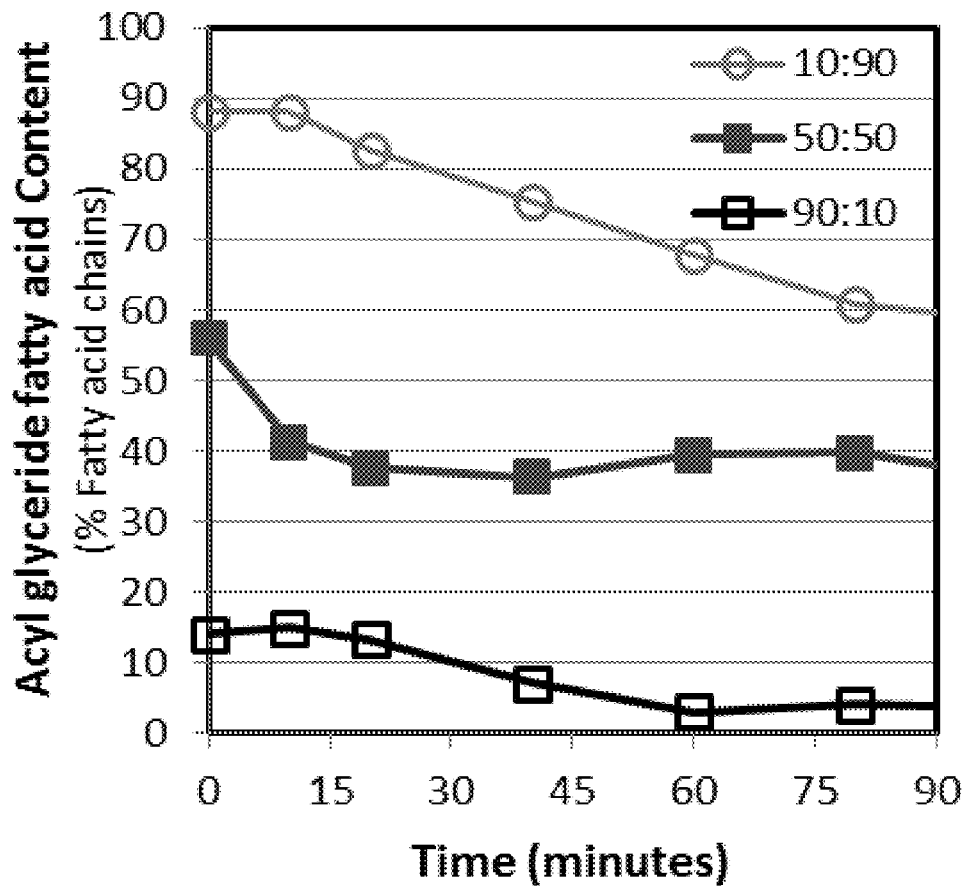
FIG. 4D shows the content of acyl glyceride in the lipid over time in the same experiment of FIG. 4A.

FIG. 4C shows the FAME content in the lipid during the reactions as measured by NMR. The FAME content begins at zero and increases in all reactions until it reaches a plateau value, which varies depending on initial FFA content in the lipid. The FAME content for reactions with high FFA contents plateaued above 90%, while reactions with equal parts FFA and TAG (50:50) plateaued near 60% FAME. The reactions with an initial FFA concentration of 10% plateaued at only about 40% FAME. Although the FFA content (acid number from FIG. 4A) fell to zero, not all fatty acids were converted to FAME. These results indicate that the transesterification reaction is incomplete, and some fatty acid chains in the reactor remain as acylglycerides: TAG, DAG, and MAG. This indicates that under the conditions of this reaction with an acid catalyst, the rate of transesterification is significantly slower than esterification. Additional experiments that utilized an alcohol feed diluted with up to 20% water (not shown here) produced FAME formation rates similar to those seen in FIG. 4C. This indicates that hydrolysis of acylglycerides to FFA is also slow under these experimental conditions.

Example 3

Figures 5A, 5B:
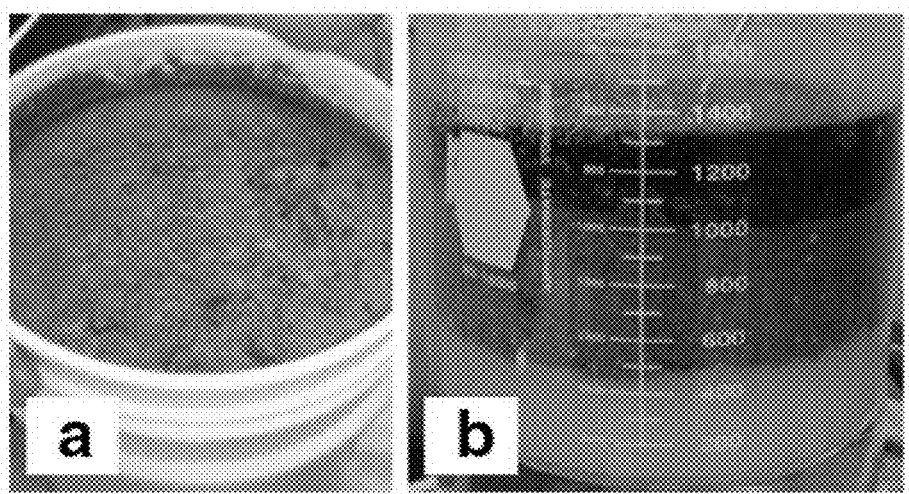
FIGS. 5A-5D show various stages of trap grease before, during and after esterification of FFA in the trap grease in a bubble column reactor according to one embodiment of the present invention.
Figures 5C, 5D:
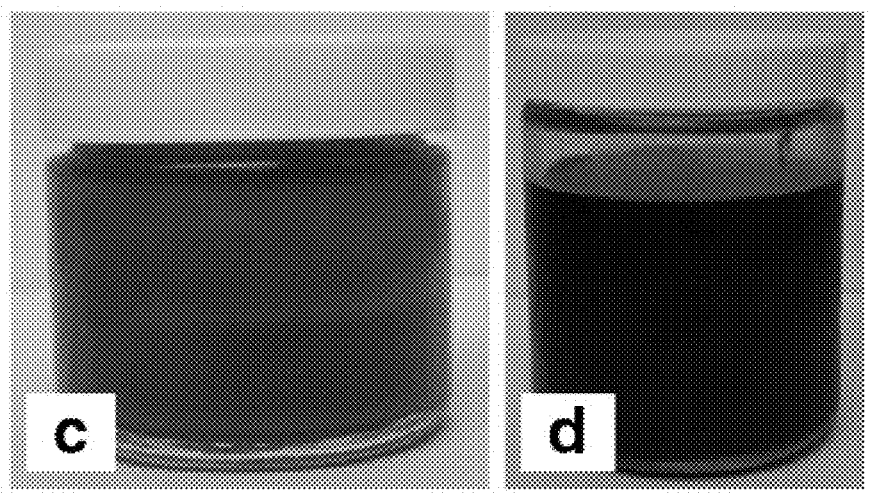

Trap grease samples (FIG. 5A) from Russell Reid, a commercial waste management company, were heated and gently stirred in this example. The heating allowed the lipid, water, and sediment layers to separate (FIG. 5B) so that the lipid layer could be collected and filtered (FIG. 5C). Once filtered, the trap grease lipids were used as a lipid feedstock in a bubble column reactor and converted into FAME (FIG. 5D) using sulfuric acid and occasionally para-toluene sulfonic acid (PTSA) as catalysts. The FAME produced had a visibly lower viscosity than the lipid layer of the trap grease. Also, although the trap grease lipids solidified at room temperature, the crude FAME produced from those lipids remained a liquid at temperatures below 10° C.

Figure 5E:
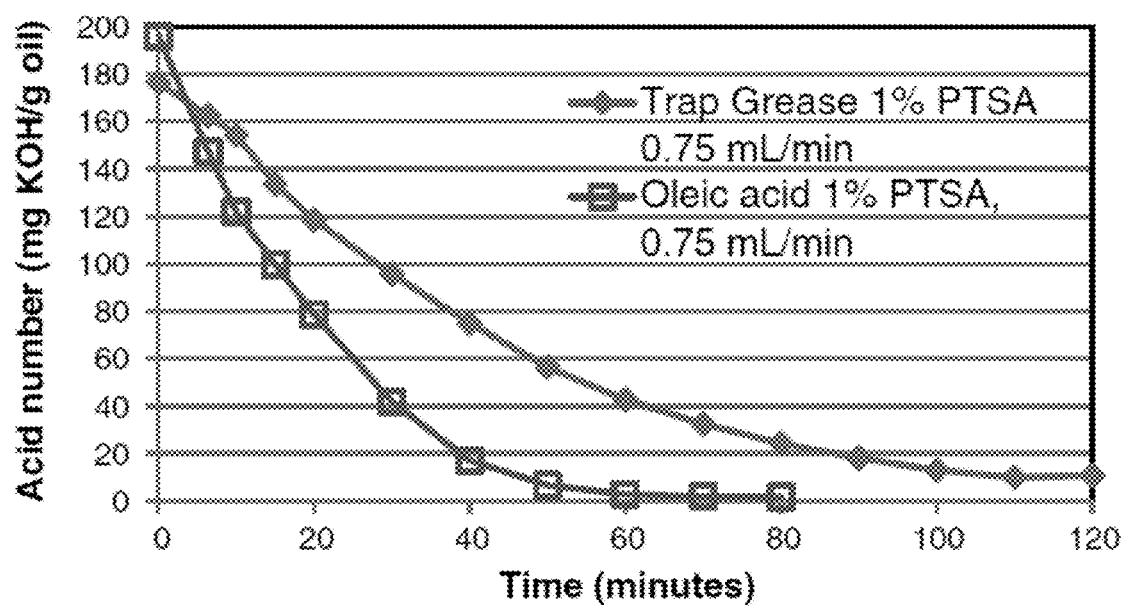
FIG. 5E shows changes in acid number over time in the lipid layer of trap grease in bubble column reactor, as compared with oleic acid reaction results. The data is from the same experiment of FIGS. 5A-5D.

FIG. 5E displays the conversion of FFA from trap grease to FAME over time. The conversion data for oleic acid is shown for comparison. The conversion of the trap grease lipids to FAME was roughly 50% slower than pure oleic acid with approximately 95% conversion achieved in about 110 min, while it took about 50 min for the pure oleic acid to achieve the same conversion. Additionally, it was observed during experiments that the typical 0.1% (w/w) acid catalyst was not sufficient for the esterification of trap grease lipids. Instead, 1% (w/w) catalyst was used for the trap grease lipids shown in FIG. 5E. The need for higher catalyst concentration suggests that there may be a contaminant in the trap grease that consumes the acid catalyst before the esterification reactions can proceed significantly.

Example 4

Other types of waste greases have also been processed by a bubble column reactor according to an embodiment of the present invention. The results of these experiments are given in Table 2 below. Each row in Table 2 corresponds to different waste grease samples that were converted to biodiesel. The first column of Table 2 indicates whether the corresponding sample was lipids extracted from grease trap waste (GTW) or sewage scum grease (SSG). The second column indicates the method used to separate the biodiesel (fatty acid methyl ester) fraction from heavy residuals by either wiped film evaporation (WFE) or rotary evaporation (rotovap). The third, fourth and fifth column related the temperature and pressure conditions used during the vacuum evaporation process.

In these experiments two vacuum evaporation steps were used with an initial condensate collected at lower temperatures and a distillate fraction collected at higher temperatures, where the residue fraction did not evaporate. The last five columns of Table 2 display sulfur contents of the initial lipids, the crude FAME after reaction and washing, and the products of the vacuum evaporation purification step: the condensate collected at lower temperatures, the distillate collected at higher temperatures, and the residue sulfur which did not evaporate (remains in the heavy residuals). These results show that the sulfur content decreased by 30-75% during the esterification reactions and washing of crude FAME. The sulfur was further reduced by vacuum evaporation to produce a distillate containing between 6-80 PPM sulfur. Additional reductions in sulfur content may be achieved by optimizing the vacuum evaporation conditions.

TABLE 2

Results of processing different types of waste greases.

| Grease Type | Purification Method | Vacuum (mBar) | Max Temp. Condensate (° C.) | Max Temp. of Distillate (° C.) | Yield of Distillate | Yield of Residue | Starting Lipid PPM Sulfur | Washed FAME PPM Sulfur | Distillate PPM Sulfur | Residue PPM Sulfur |
|---|---|---|---|---|---|---|---|---|---|---|
| GTW | WFE | 1.3 | 115 | 190 | 52% | 22% | 230 | 157 | 15 | 356 |
| GTW | WFE | 1.3 | 120 | 190 | 93% | 6% | 96 | 65 | 10 | 393 |
| SSG | WFE | 1.3 | 120 | 190 | 78% | 12% | 429 | 259 | 87 | 439 |
| GTW | WFE | 1.3 | 120 | 190 | 81% | 19% | N/A | N/A | 27.2 | N/A |
| GTW | WFE | 1.3 | 120 | 190 | 69% | 31% | N/A | N/A | 17.6 | N/A |
| GTW | WFE | 1.3 | 120 | 190 | 92% | 8% | N/A | N/A | 15.0 | N/A |
| GTW | VacEvap | 4 | N/A | 200 | 76% | 24% | N/A | 118 | 15.1 | 434 |
| GTW | Rotovap | 5 | N/A | 195 | 76% | 24% | 409 | 183 | N/A | N/A |
| GTW | Rotovap | 3 | 180 | 198 | 81% | 17% | 409 | 183 | 18.0 | N/A |
| GTW | Rotovap | 1 | 175 | 194 | 83% | 10% | 303 | N/A | 19.9 | N/A |
| GTW | Rotovap | 2 | 172 | 200 | 75% | 15% | 303 | 80 | 12.3 | 416 |
| GTW | WFE | 1.3 | 120 | 190 | 82% | 18% | 303 | 80 | 26.0 | 1189 |
| GTW | WFE | 1.3 | 120 | 160 | 55% | 44% | 409 | 183 | 5.8 | 224 |
| GTW | WFE | 1.3 | 120 | 190 | 94% | 5% | 409 | 183 | 14.3 | 751 |
| SSG | Rotovap | 1.3 | N/A | 200 | 33% | 10% | 474 | 143 | 76 | 474 |

The results of Example 4 are summarized in Table 3 below. Table 3 summarizes the ranges of sulfur content observed for samples at different stages of converting waste greases to biodiesel. For sewage scum grease (SSG), the average sulfur content was reduced by 55% from the waste grease to the reacted and washed FAME and by 82% from the waste grease to distilled biodiesel. For grease trap waste (GTW), the sulfur average content was reduced by 58% from the waste grease to reacted and washed FAME and by 95% from the waste grease to distilled biodiesel. These are typical results and it should be understood that the actual sulfur content depends upon many factors including the composition of the starting lipids, reaction conditions, washing processes used, and purification conditions.

TABLE 3

Reduction of sulfur content by the method of the present invention.

| | SSG Avg | Std Dev | GTW Avg | Std Dev | GTW Outlier |
|---|---|---|---|---|---|
| Lipids | 453 | 23 | 347 | 71 | 96 |
| Washed FAME | 201 | 82 | 146 | 46 | 65 |
| Residue | 457 | 25 | 595 | 339 | 393 |
| Condensate | 41 | 12 | 89 | 0 | 22 |
| Distillate | 82 | 8 | 17 | 6 | 10 |

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

Throughout this application, various publications are referenced. The disclosures of these publications in their entireties are hereby incorporated by reference into this application in order to more fully describe the state of the art as known to those skilled therein as of the date of the disclosure described and claimed herein.

REFERENCES

[1] J. Van Gerpen, Biodiesel processing and production, Fuel Processing Technology 86 (2005) 1097-1107.
[2] K. S. Tyson, J. Bozell, R. Wallace, E. Petersen, L. Moens, Biomass Oil Analysis: Research Needs and Recommendations, NREL, Golden Colo., 2004.
[3] A. A. Apostolakou, I. K. Kookos, C. Marazioti, K. C. Angelopoulos, Techno-economic analysis of a biodiesel production process from vegetable oils, Fuel Processing Technology 90 (2009) 1023-1031.
[4] M. Haas, Improving the economics of biodiesel production through the use of low value lipids as feedstocks: vegetable oil soapstock, Fuel Processing Technology 86 (2005) 1087-1096.
[5] J. M. Marchetti, V. U. Miguel, A. F. Errazu, Techno-economic study of different alternatives for biodiesel production, Fuel Processing Technology 89 (2008) 740-748.
[6] Y. Zhang, Biodiesel production from waste cooking oil: 1. Process design and technological assessment, Bioresource Technology 89 (2003) 1-16.

[7] Y. Zhang, M. A. Dube, D. D. McLean, M. Kates, Biodiesel production from waste cooking oil: 2. Economic assessment and sensitivity analysis, Bioresource Technology 90 (2003) 229-240.

[8] D. Samios, F. Pedrotti, A. Nicolau, Q. B. Reiznautt, D. D. Martini, F. M. Dalcin, A transesterification double step process—TDSP for biodiesel preparation from fatty acids triglycerides, Fuel Processing Technology 90 (2009) 599-605.

[9] S. V. Ghadge, H. Raheman, Biodiesel production from mahua (*Madhuca indica*) oil having high free fatty acids, Biomass and Bioenergy 28 (2005) 601-605.

[10] A. N. A. Aryee, F. R. van de Voort, B. K. Simpson, FTIR determination of free fatty acids in fish oils intended for biodiesel production, Process Biochemistry 44 (2009) 401-405.

[11] M. G. Varanda, G. Pinto, F. Martins, Life cycle analysis of biodiesel production, Fuel Processing Technology 92 (2011) 1087-1094.

[12] M. Berrios, J. Siles, M. Martin, A. Martin, A kinetic study of the esterification of free fatty acids (FFA) in sunflower oil, Fuel 86 (2007) 2383-2388.

[13] T. Kocsisova, J. Cvengro, J. Lutisan, High-temperature esterification of fatty acids with methanol at ambient pressure, European Journal of Lipid Science and Technology 107 (2005) 87-92.

[14] I. L. Lucena, R. M. A. Saboya, J. F. G. Oliveira, M. L. Rodrigues, A. E. B. Torres, C. L. Cavalcante, E. J. S. Parente, G. F. Silva, F. A. N. Fernandes, Oleic acid esterification with ethanol under continuous water removal conditions, Fuel 90 (2011) 902-904.

[15] E. Santacesaria, R. Tesser, M. Di Serio, M. Guida, D. Gaetano, A. Garcia Agreda, F. Cammarato, Comparison of different reactor configurations for the reduction of free acidity in raw materials for biodiesel production, Industrial & Engineering Chemistry Research 46 (2007) 8355-8362.

[16] F. A. P. Voll, C. da Silva, C. C. R. S. Rossi, R. Guirardello, F. de Castilhos, J. V. Oliveira, L. Cardozo-Filho, Thermodynamic analysis of fatty acid esterification for fatty acid alkyl esters production, Biomass and Bioenergy 35 (2011) 781-788.

[17] Z.-M. Wang, J.-S. Lee, J.-Y. Park, C.-Z. Wu, Z.-H. Yuan, Optimization of biodiesel production from trap grease via acid catalysis, Korean Journal of Chemical Engineering 25 (2008) 670-674.

[18] B. D. Wahlen, B. M. Barney, L. C. Seefeldt, Synthesis of biodiesel from mixed feedstocks and longer chain alcohols using an acid-catalyzed method, Energy & Fuels 22 (2008) 4223-4228.

[19] USDA, National Weekly Ag Energy Round-Up, USDA Livestock, Poultry & Grain Market News, United States Department of Agriculture, Des Moines, Iowa, 2014.

[20] DELCORA, Resolution NO. 2013-21, Hauled Waste Rates, Delaware County Regional Water Control Authority, Chester, P A, 2013.

[21] M. Canakci, The potential of restaurant waste lipids as biodiesel feedstocks, Bioresource Technology 98 (2007) 183-190.

[22] K. S. Tyson, DOE analysis of fuels and coproducts from lipids, Fuel Processing Technology 86 (2005) 1127-1136.

[23] W. W. Berry, B. J. Ratigan, Process of making alkyl esters of free fatty acids, Philadelphia Fry-o-Diesel Inc., US, 2010.

[24] ASTM, Standard Test Method for Acid Number of Petroleum Products by Potentiometric Titration, in, ASTM International, West Conshohocken, Pa.

[25] AOCS, Acid Value, in: AOCS Methods for Biodiesel Feedstock Quality, American Oil Chemists Society, Urbana, Ill.

What is claimed is:

1. A method of producing fatty acid alkyl esters from a lipid, comprising steps of:
    introducing a gas comprising vapor containing an alcohol into the lipid in a bubble column reactor in a form of bubbles to enable the bubbles to pass through the lipid and be discharged from the lipid; and
    adding an alcohol solution of an acid catalyst to the lipid in the bubble column reactor.

2. The method of claim 1, wherein the alcohol contained in the vapor is selected from the group consisting of methanol and ethanol.

3. The method of claim 1, wherein the alcohol contained in the vapor is selected from the group consisting of 1-propanol, iso-propanol and butanols.

4. The method of claim 2, wherein the lipid is at least one selected from waste fats, waste greases and waste oils.

5. The method of claim 2, wherein the lipid is a portion of a trap grease.

6. The method of claim 2, wherein the lipid has a content of fatty acids of at least about 10%, or at least about 50% or at least about 90%.

7. The method of claim 2, wherein the bubbles strip water from the lipid.

8. The method of claim 2, further comprising the step of recycling the alcohol contained in the vapor in the discharged bubbles.

9. The method of claim 1, wherein the acid catalyst is at least one selected from sulfonic acid, para-toluene sulfonic acid, and sulfuric acid.

10. The method of claim 1, wherein the acid catalyst is added to the lipid in a range of from about 0.01 wt. % to about 2.0 wt. % based on the weight of the lipid.

11. The method of claim 2, wherein the alcohol contained in the vapor is introduced to the lipid at a flow rate in a range of from about 0.20 mL/min to about 3.5 mL/min.

12. The method of claim 2, wherein the introducing step is performed for a time period in a range of from about 6.2 minutes to about 113.5 minutes.

13. The method of claim 2, wherein the vapor contains up to about 10 v/v % of water, or up to 20 v/v % of water.

14. The method of claim 2, further comprising the step of heating the lipid to a temperature of 120° C.

15. The method of claim 2, further comprising the step of subjecting the product of the introducing step to a transesterification process catalyzed by a base catalyst to convert triacyl glyceride in the lipid to fatty acid alkyl esters and glycerin.

16. The method of claim 15, wherein the transesterification process uses the same alcohol used in the introducing step.

17. The method of claim 15, wherein the base catalyst is a strong base selected from sodium hydroxide and potassium hydroxide.

18. The method of claim 1, wherein the lipid is selected from trap grease, sewage scum grease, acid oils and waste materials having a free fatty acid content of greater than 40% and by-products of a process selected from rendering processes, animal processing, vegetable oil separation and refining processes, biodiesel production processes.

19. The method of claim 1, wherein the alcohol solution of an acid catalyst is gradually added to the lipid during the first five minutes of the introducing step.

20. The method of claim 2, wherein the alcohol contained in the vapor is introduced to the lipid at a flow rate in a range of from about 0.43 mL/min to about 2.57 mL/min.

* * * * *